US012629213B2

(12) United States Patent
Govari et al.

(10) Patent No.: US 12,629,213 B2
(45) Date of Patent: May 19, 2026

(54) TRACKING COORDINATES OF ELECTRODES WITH BEZIER CURVES

(71) Applicant: Biosense Webster (Israel) Ltd., Yokneam (IL)

(72) Inventors: Assaf Govari, Haifa (IL); Vadim Gliner, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 121 days.

(21) Appl. No.: 17/874,224

(22) Filed: Jul. 26, 2022

(65) Prior Publication Data

US 2024/0033008 A1     Feb. 1, 2024

(51) Int. Cl.
| | |
|---|---|
| *A61B 34/20* | (2016.01) |
| *A61B 5/00* | (2006.01) |
| *A61B 5/06* | (2006.01) |
| *A61B 5/367* | (2021.01) |
| *A61B 5/287* | (2021.01) |

(52) U.S. Cl.
CPC .............. *A61B 34/20* (2016.02); *A61B 5/062* (2013.01); *A61B 5/367* (2021.01); *A61B 5/6858* (2013.01); *A61B 5/287* (2021.01); *A61B 2034/2051* (2016.02)

(58) Field of Classification Search
CPC . A61B 2034/2051; A61B 34/20; A61B 5/062; A61B 5/287; A61B 5/367; A61B 5/6858; A61B 5/6859
See application file for complete search history.

(56) References Cited

U.S. PATENT DOCUMENTS

| | | | |
|---|---|---|---|
| 6,148,095 A | 11/2000 | Prause et al. | |
| 7,371,067 B2 | 5/2008 | Anderson et al. | |
| 2007/0018988 A1 | 1/2007 | Guthe | |
| 2008/0243063 A1 | 10/2008 | Camarillo | |
| 2012/0075310 A1 | 3/2012 | Michail et al. | |
| 2017/0086705 A1 | 3/2017 | Harlev et al. | |
| 2018/0344187 A1* | 12/2018 | Osadchy | A61B 5/367 |
| 2020/0197097 A1 | 6/2020 | Govari | |
| 2020/0397338 A1* | 12/2020 | Gliner | A61B 5/7425 |

(Continued)

OTHER PUBLICATIONS

Lonestar, "Honor Calculs I—Project II—Tangents. Tangents Everywhere", 2018 (Year: 2018).*

(Continued)

*Primary Examiner* — Brooke Lyn Klein
(74) *Attorney, Agent, or Firm* — Volpe Koenig

(57)                 ABSTRACT

A technique is described herein. The technique includes receiving endpoint location data and spline tangent data from a pair of position sensors mounted on opposite ends of a distal tip of a catheter, wherein said distal tip includes a plurality of flexible splines and a plurality of electrodes disposed on each of the flexible splines and wherein said endpoint location data and spline tangent data is received while said distal tip is positioned within a heart chamber; based on said endpoint location data and spline tangent data, calculating Bezier curve control points; based on the Bezier curve control points, determining estimated positions of said plurality of electrodes; and updating an electro-anatomical map of said heart chamber that is rendered on a display based on the estimated positions determined.

20 Claims, 7 Drawing Sheets

(56) References Cited

U.S. PATENT DOCUMENTS

2021/0059608 A1* 3/2021 Beeckler ............... A61B 5/065

OTHER PUBLICATIONS

Extended European Search Report issued on Nov. 23, 2023 for European Patent Application No. 23187410.8.
Communication Pursuant to Article 94(3) EPC issued on Apr. 5, 2024 for European Patent Application No. 23187410.8.
Liu, D., et al., "B-Spline-Based Sharp Feature Preserving Shape Reconstruction Approach for Electrical Impedance Tomography", IEEE Transactions on Medical Imaging, USA, (2019).

* cited by examiner

700

701  Retrieve mechanical parameters of system

702  Receive endpoint location data and deflection angle in mapping software

704  Process endpoint location data and deflection angle to calculate bezier curve control points 706  Output data indicating estimated spline shape and position and/or estimated electrode position

TRACKING COORDINATES OF ELECTRODES WITH BEZIER CURVES

BACKGROUND

Treatments for cardiac conditions often require obtaining a detailed mapping of cardiac tissue, chambers, veins, arteries and/or electrical pathways. Effective techniques for obtaining such mappings are constantly being improved.

SUMMARY

A technique is described herein. The technique includes receiving endpoint location data and spline tangent data from a pair of position sensors mounted on opposite ends of a distal tip of a catheter, wherein said distal tip includes a plurality of flexible splines and a plurality of electrodes disposed on each of the flexible splines and wherein said endpoint location data and spline tangent data is received while said distal tip is positioned within a heart chamber, based on said endpoint location data and spline tangent data, calculating Bezier curve control points (506); based on the Bezier curve control points (506), determining estimated positions of said plurality of electrodes (111); and; updating an electro-anatomical map of said heart chamber that is rendered on a display based on the estimated positions determined.

According to one or more embodiments, the exemplary technique above can be implemented as a method, an apparatus, a system, and/or a computer program product. In some examples, the endpoint location data comprises locations of proximal and distal ends (302, 304) of a distal tip of a catheter, e.g., catheter basket (116). In some examples, the spline tangent data includes information indicating a tangent of a proximal end of a spline (109) of the catheter basket (116). In some examples, calculating the Bezier curve control points (506) includes determining the Bezier curve control points (506) based on distance between endpoints of the spline (109) and on the spline tangent data (309). In some examples, determining the estimated electrode (111) positions comprises determining shapes and positions of splines (109) of the catheter (116) and determining estimated electrode (111) positions based on the shapes and positions of the splines (109). Some examples further include generating geometry points (504) based on the Bezier curve control points (506). In some examples, not all Bezier curve control points (506) lie on the estimated spline (109) shape. In some examples, the calculating and determining are performed by software executing in a processor. In some examples, the endpoint location (302, 304) data is received from a central processing unit.

A system is provided. The system includes a console configured to receive endpoint location data and spline tangent data from a pair of position sensors mounted on opposite ends (302, 304) of a distal tip of a catheter, wherein said distal tip includes a plurality of flexible splines (109) and a plurality of electrodes (111) disposed on each of the flexible splines and wherein said endpoint location data and spline tangent data is received while said distal tip is positioned within a heart chamber; a processor configured to: based on said endpoint (302, 304) location data and spline tangent data (309), calculate Bezier curve control points (506), and based on the Bezier curve control points, determine estimated positions of said plurality of electrodes (111); and a display configured to display an electro-anatomical map of said heart chamber based on the estimated positions determined.

In some examples, the endpoint (302, 304) location data comprises locations of proximal and distal ends (302, 304) of the catheter basket. In some examples the spline tangent (309) data includes information indicating a tangent of a proximal end of a spline of the catheter basket. In some examples, calculating the Bezier curve control points (506) includes determining the Bezier curve control points based on distance between endpoints (302, 304) of the spline and on the spline tangent data. In some examples, determining the estimated electrode (111) positions comprises determining shapes and positions of splines (109) of the catheter and determining estimated electrode (111) positions based on the shapes and positions of the splines (109). In some examples, the processor is further configured to generate geometry points (504) based on the Bezier curve control points (506). In some examples, not all Bezier curve control points (506) lie on the estimated spline (109) shape. In some examples, the calculating and determining are performed by software executing in a processor. In some examples, the endpoint location data is received from a central processing unit.

A non-transitory computer-readable medium storing instructions is described herein. The instructions, when executed by a processor, cause the processor to perform operations comprising: receiving endpoint location data and spline tangent data from a pair of position sensors mounted on opposite ends of a distal tip of a catheter, wherein said distal tip includes a plurality of flexible splines and a plurality of electrodes disposed on each of the flexible splines and wherein said endpoint location data and spline tangent data is received while said distal tip is positioned within a heart chamber, based on said endpoint location data and spline tangent data, calculating Bezier curve control points (506); based on the Bezier curve control points (506), determining estimated positions of said plurality of electrodes (111); and; updating an electro-anatomical map of said heart chamber that is rendered on a display based on the estimated positions determined.

In some examples, the endpoint (302, 304) location data comprises locations of proximal and distal ends (302, 304) of the catheter basket (116). In some examples, the spline (109) tangent (309) data includes information indicating a tangent of a proximal end (302) of a spline (109) of the catheter basket (116). In some examples, calculating the Bezier curve control points (506) includes determining the Bezier curve control points (506) based on distance between endpoints (302, 304) of the spline (109) and on the spline tangent data (309). In some examples, determining the estimated electrode (111) positions comprises determining shapes and positions of splines (109) of the catheter (110) and determining estimated electrode positions (111) based on the shapes and positions of the splines (109). In some examples, the operations further comprise generating geometry points (504) based on the Bezier curve control points (506). In some examples, not all Bezier curve control points (506) lie on the estimated spline (109) shape. In some examples, the calculating and determining are performed by software executing in a processor. In some examples, the endpoint location data is received from a central processing unit.

BRIEF DESCRIPTION OF THE DRAWINGS

A more detailed understanding may be had from the following description, given by way of example in conjunction with the accompanying drawings, wherein like reference numerals in the figures indicate like elements, and wherein.

DETAILED DESCRIPTION

A technique is described herein. The technique includes processing endpoint location data and spline tangent data for a catheter to calculate Bezier curve control points; and based on the Bezier curve control points, determining estimated electrode positions for the catheter.

Figure 1:
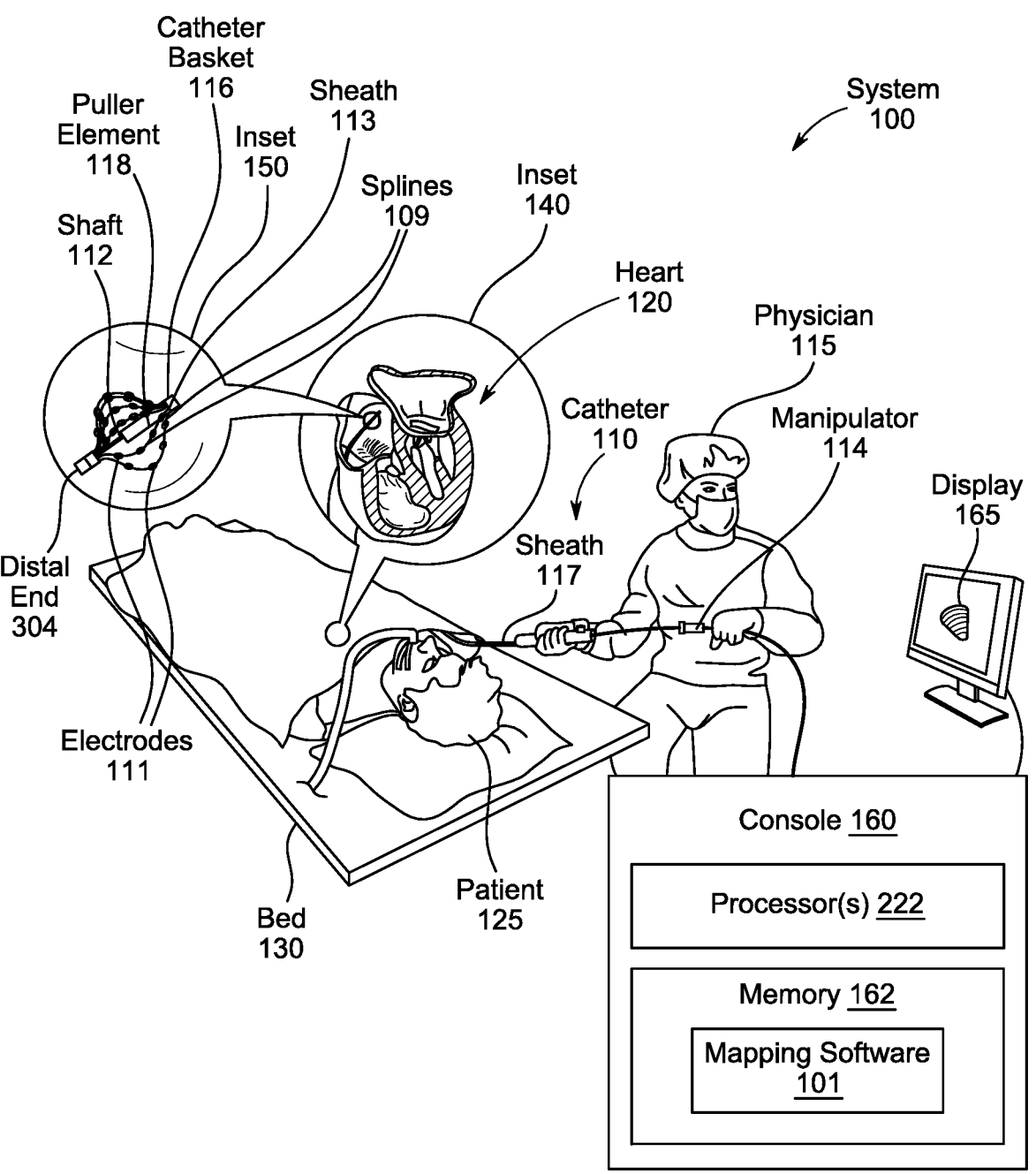
FIG. 1 illustrates a diagram of an exemplary system in which one or more features of the disclosure subject matter can be implemented according to one or more embodiments.

FIG. 1 is a diagram of an example system (e.g., medical device equipment), shown as a system 100, in which one or more features of the subject matter herein can be implemented according to one or more embodiments. All or part of the system 100 can be used to detect, diagnose, and/or treat cardiac conditions.

The system 100, as illustrated, includes a catheter 110, which includes a manipulator 114, a shaft 112 disposed through a sheath 113, and a distal tip in the shape of a basket (referred to herein as a "catheter basket" 116). The catheter basket 116 includes a plurality of electrodes 111 disposed on a plurality of bendable splines 109. A puller element 118 pulls or pushes the distal end 304 of the catheter basket 116, expanding or collapsing the catheter basket 116. In some examples, the catheter basket 116 includes one or more position sensors that allow sensing of the position of the proximal end and distal end of the catheter basket 116. Also illustrated in FIG. 1 are a physician 115 (or a medical professional, technician, clinician, etc.), a heart 120, a patient 125, and a bed 130 (or a table). Note that insets 140 and 150 show the heart 120 and the catheter 110 in greater detail. The system 100 also, as illustrated, includes a console 160 (including one or more processors 222 and memories 162 providing controlling and processing capability) and a display 165. Note further each element and/or item of the system 100 is representative of one or more of that element and/or that item. The example of the system 100 shown in FIG. 1 can be modified to implement the embodiments disclosed herein. The disclosed embodiments can similarly be applied using other system components and settings. Additionally, the system 100 can include additional components, such as elements for sensing electrical activity, wired or wireless connectors, processing and display devices, or the like.

The system 100 can be utilized to detect, diagnose, and/or treat cardiac conditions. Cardiac conditions, such as cardiac arrhythmias, persist as common and dangerous medical ailments, especially in the aging population. For instance, the system 100 can be part of a surgical system (e.g., CARTO® system sold by Biosense Webster) that is configured to obtain biometric data (e.g., anatomical and electrical measurements of a patient's organ, such as the heart 120) and perform a cardiac ablation procedure. According to one or more embodiments, the biometric data can include anatomical and electrical measurements acquired in a significant portion of an atrium during the mapping and ablation procedures.

More particularly, treatments for cardiac conditions such as cardiac arrhythmia often require obtaining a detailed mapping of cardiac tissue, chambers, veins, arteries and/or electrical pathways. For example, a prerequisite for performing a catheter ablation (as described herein) successfully is that the cause of the cardiac arrhythmia is accurately located in a chamber of the heart 120. Such locating may be done via an electrophysiological investigation during which electrical potentials are detected and spatially resolved with a mapping catheter (e.g., the catheter 110) introduced into the chamber of the heart 120. This electrophysiological investigation, the so-called electro-anatomical mapping, thus provides 3D mapping data which can be displayed on a monitor. In many cases, the mapping function and a treatment function (e.g., ablation) are provided by a single catheter or group of catheters such that the mapping catheter also operates as a treatment (e.g., ablation) catheter at the same time. Mapping software 101 interfaces with catheter 110 to perform the mapping operations as described in further detail herein.

In support of the system 100 detecting, diagnosing, and/or treating cardiac conditions, the catheter 110 can be navigated by the physician 115 into the heart 120 of the patient 125 lying on the bed 130. For instance, the physician 115 can insert the shaft 112 through the sheath 113, while manipulating a distal end 304 of the catheter basket 116 using the manipulator 114. The catheter 110 can be inserted through the sheath 113 in a collapsed state and can be then expanded within the heart 120.

Generally, electrical activity at a point in the heart 120 may be typically measured by advancing the catheter 110 to that point in the heart 120, contacting the tissue with the one or more electrodes 111 and acquiring data at that point.

The catheter 110, includes a plurality of flexible splines 109 and a plurality of electrodes 111 disposed on each of the flexible splines 109. The catheter 110 is configured to obtain biometric data, such as electrical signals of an intra-body organ (e.g., the heart 120), and/or to ablate tissue areas of thereof (e.g., a cardiac chamber of the heart 120). Note that the electrodes 111 are representative of any like elements, such as metallic elements, tracking coils, piezoelectric transducer, electrodes, or combination of elements configured to ablate the tissue areas or to obtain the biometric data.

Biometric data (e.g., patient biometrics, patient data, or patient biometric data) can include one or more of local activation times (LATs), electrical activity, topology, bipolar mapping, reference activity, ventricle activity, dominant frequency, impedance, or the like. The LAT can be a point in time of a threshold activity corresponding to a local activation, calculated based on a normalized initial starting point. Electrical activity can be any applicable electrical signals that can be measured based on one or more thresholds and can be sensed and/or augmented based on signal to noise ratios and/or other filters. A topology can correspond to the physical structure of a body part or a portion of a body part and can correspond to changes in the physical structure relative to different parts of the body part or relative to different body parts.

Examples of biometric data include, but are not limited to, patient identification data, IC ECG data, bipolar intracardiac reference signals, anatomical and electrical measurements, trajectory information, body surface (BS) ECG data, historical data, blood pressure data, ultrasound signals, radio signals, audio signals, a two- or three-dimensional image data, blood glucose data, and temperature data. The biometrics data can be used, generally, to monitor, diagnosis, and treatment any number of various diseases, such as cardiovascular diseases (e.g., arrhythmias, cardiomyopathy, and coronary artery disease) and autoimmune diseases (e.g., type I and type II diabetes). Note that BS ECG data can include data and signals collected from electrodes on a surface of a patient, IC ECG data can include data and signals collected from electrodes within the patient, and ablation data can include data and signals collected from tissue that has been ablated. Further, BS ECG data, IC ECG data, and ablation data, along with catheter electrode position data, can be derived from one or more procedure recordings.

For example, the catheter 110 can use the electrodes 111 to implement intravascular ultrasound and/or Mill catheterization to image the heart 120 (e.g., obtain and process the biometric data). Inset 150 shows the catheter 110 in an enlarged view, inside a cardiac chamber of the heart 120.

The catheter 110 is a basket catheter. The basket catheter can be designed such that when deployed into a patient's body, its electrodes can be held in intimate contact against an endocardial surface. As an example, a basket catheter can be inserted into a lumen, such as a pulmonary vein ("PV"). The basket catheter can be inserted into the PV with proximal end at maximal distance from distal end, such that the basket catheter does not occupy its maximum volume while being inserted into the PV. The basket catheter can expand by moving proximal end towards distal end while inside the PV, such that those electrodes on the basket catheter are in contact with an entire circular section of the PV. Such contact with an entire circular section of the PV, or any other lumen, can enable efficient imaging and/or ablation.

According to other examples, body patches and/or body surface electrodes may also be positioned on or proximate to a body of the patient 125. The catheter 110 with the one or more electrodes 111 can be positioned within the body (e.g., within the heart 120) and a position of the catheter 110 can be determined by the system 100 based on signals transmitted and received between positions sensors of the catheter 110 and the body patches and/or body surface electrodes. Additionally, the electrodes 111 can sense the biometric data from within the body of the patient 125, such as within the heart 120 (e.g., the electrodes 111 sense the electrical potential of the tissue in real time). The biometric data can be associated with the determined position of the catheter 110 such that a rendering of the patient's body part (e.g., the heart 120) can be displayed and show the biometric data overlaid on a shape of the body part. The mapping software 101 assists with determining position of the electrodes 111, to assist with obtaining the biometric data.

The catheter 110 and other items of the system 100 can be connected to the console 160. The console 160 can include any computing device, which employs the mapping software 101. According to an exemplary embodiment, the console 160 includes the one or more processors 222 (any computing hardware) and the memory 162 (any non-transitory tangible media), where the one or more processors 222 execute computer instructions with respect to the mapping software 101 and the memory 162 stores these instructions for execution by the one or more processors 222. For instance, the console 160 can be configured to receive and/or store the biometric data on a database of the memory 162, process the biometric data, and determine if a given tissue area conducts electricity.

In an example, the console 160 can be any computing device, as noted herein, including software (e.g., the mapping software 101) and/or hardware (e.g., the processor 222 and the memory 162), such as a general-purpose computer, with suitable front end and interface circuits for transmitting and receiving signals to and from the catheter 110, as well as for controlling the other components of the system 100. For example, the front end and interface circuits include input/output (I/O) communication interfaces that enables the console 160 to receive signals from and/or transfer signals to the at least one electrode 111. The console 160 can include real-time noise reduction circuitry typically configured as a field programmable gate array (FPGA), followed by an analog-to-digital (A/D) ECG or electrocardiograph/electromyogram (EMG) signal conversion integrated circuit. The console 160 can pass the signal from an A/D ECG or EMG circuit to another processor and/or can be programmed to perform one or more functions disclosed herein.

The display 165, which can be any electronic device for the visual presentation of the biometric data, is connected to the console 160. According to an exemplary embodiment, during a procedure, the console 160 can facilitate on the display 165 a presentation of a body part rendering to the physician 115 and store data representing the body part rendering in the memory 162. For instance, maps depicting motion characteristics can be rendered/constructed based on the trajectory information sampled at a sufficient number of points in the heart 120. As an example, the display 165 can include a touchscreen that can be configured to accept inputs from the physician 115, in addition to presenting the body part rendering.

In some embodiments, the physician 115 can manipulate the elements of the system 100 and/or the body part rendering using one or more input devices, such as a touch pad, a mouse, a keyboard, a gesture recognition apparatus, or the like. For example, an input device can be used to change a position of the catheter 110, such that rendering is updated. Note that the display 165 can be located at a same location or a remote location, such as a separate hospital or in separate healthcare provider networks.

In one example, to obtain electrode position data for the electrodes 111, the console 160 can be connected, by a cable, to body surface ("BS") electrodes, which include adhesive skin patches affixed to the patient 125. More particularly, the processor 222 can determine position coordinates of the electrodes 111 inside the body part (e.g., the heart 120) of the patient 125. The position coordinates may be based on impedances or electromagnetic fields measured between the body surface electrodes and the electrode 111 of the catheter 110 or other electromagnetic components such as position sensors disposed within the catheter basket 116. Additionally, or alternatively, location pads, which generate magnetic fields used for navigation, may be located on a surface of the bed 130 and may be separate from the bed 130. The biometric data can be transmitted to the console 160 and stored in the memory 162. Alternatively, or in addition, the biometric data may be transmitted to a server, which may be local or remote, using a network as further described herein.

According to one or more exemplary embodiments, the catheter 110 may be configured to ablate tissue areas of a cardiac chamber of the heart 120. For instance, ablation electrodes, such as the at least one electrode 111, may be configured to provide energy to tissue areas of an intra-body organ (e.g., the heart 120). The energy may be thermal energy and may cause damage to the tissue area starting from the surface of the tissue area and extending into the thickness of the tissue area. The biometric data with respect to ablation procedures (e.g., ablation tissues, ablation locations, etc.) can be considered ablation data.

A catheter ablation-based treatment may include mapping the electrical properties of heart tissue, especially the endocardium and the heart volume, and selectively ablating cardiac tissue by application of energy. Electrical or cardiac mapping (e.g., implemented by any electrophysiological cardiac mapping system and technique described herein) includes creating a map of electrical potentials (e.g., a voltage map) of the wave propagation along the heart tissue or a map of arrival times (e.g., a LAT map) to various tissue located points. Electrical or cardiac mapping (e.g., a cardiac map) may be used for detecting local heart tissue dysfunction. Ablations, such as those based on cardiac mapping, can cease or modify the propagation of unwanted electrical signals from one portion of the heart 120 to another.

The ablation process damages the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. Another example of an energy delivery technique includes irreversible electroporation (IRE), which provides high electric fields that damage cell membranes. In a two-step procedure (e.g., mapping followed by ablation) electrical activity at points within the heart 120 is typically sensed and measured by advancing the catheter 110 containing one or more electrical sensors (e.g., electrodes 111) into the heart 120 and obtaining/acquiring data at a multiplicity of points (e.g., as biometric data generally, or as ECG data specifically). This ECG data is then utilized to select the endocardial target areas, at which ablation is to be performed. The mapping software 101 assists with these steps by estimating position of the electrodes 111.

Among other things, the mapping software 101 maps position of the electrodes 111 of the catheter 110. The catheter 110 has position tracking elements on proximal and distal ends of the catheter basket 116, but the electrodes 111 themselves do not have associated position sensors. Further, the electrodes 111 are disposed on flexible splines 109 which bend based both on relative positions of the proximal and distal ends of the catheter basket 116 as well as deflection of the entire catheter 110 with respect to the shaft 112. Thus, the mapping software 101 performs operations to determine the shape and positions of the splines 109 based on the detected positions and orientations of the proximal and distal ends of the catheter basket 116 as well as the deflection angle of the catheter basket 116. The mapping software 101 generates Bezier curves to represent the shape, position, and/or deflection of the splines 109 and obtains positions of the electrodes 111 based on the shape, position, and/or deflection. Additional details follow.

Figure 2:
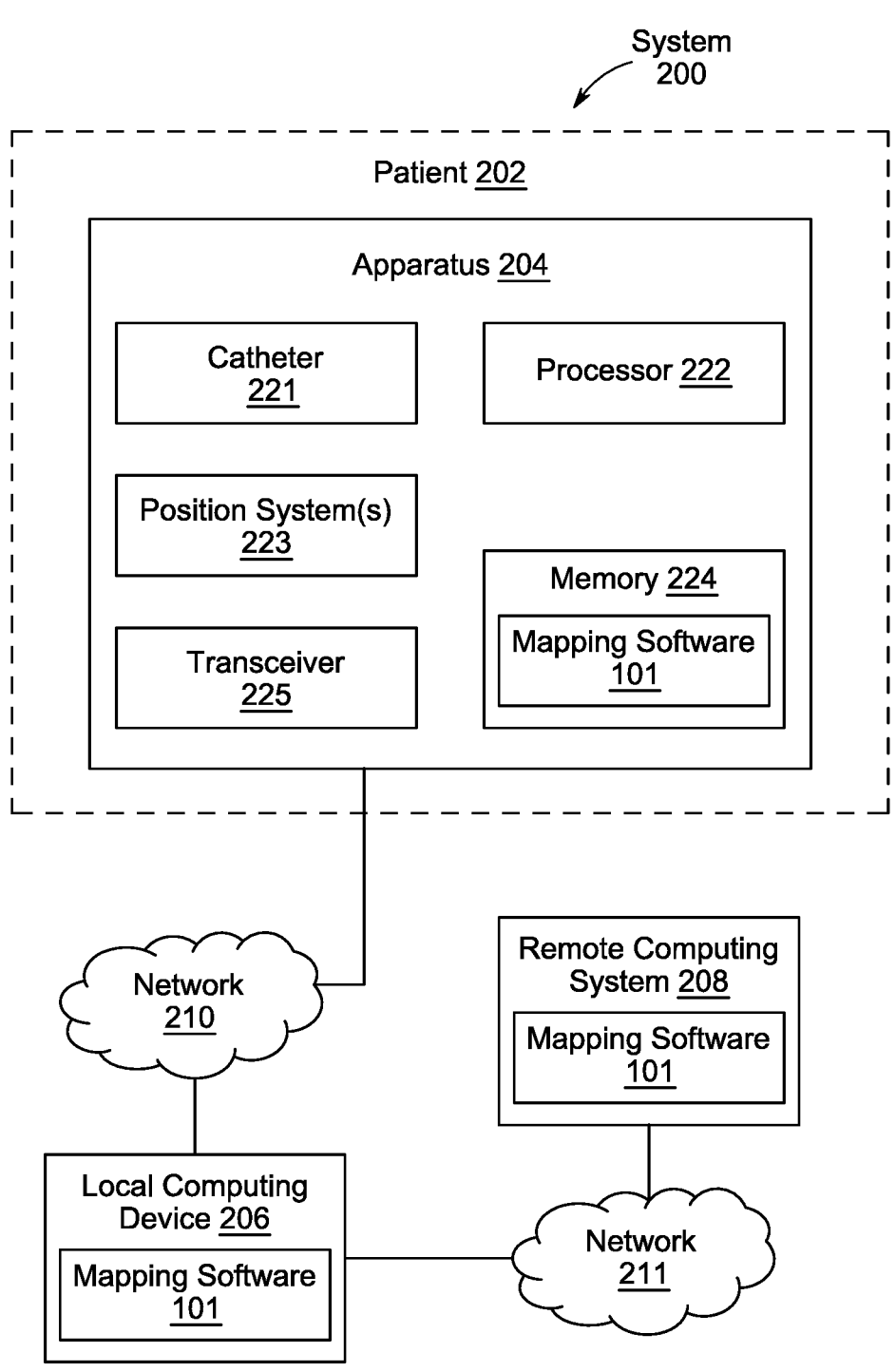
FIG. 2 illustrates a system in which one or more features of the disclosure subject matter can be implemented, according to an example.

Turning now to FIG. 2, a diagram of a system 200 in which one or more features of the disclosed subject matter can be implemented is illustrated according to one or more exemplary embodiments. The system 200 includes, in relation to a patient 202 (e.g., an example of the patient 125 of FIG. 1), an apparatus 204, a local computing device 206, a remote computing system 208, a first network 210, and a second network 211. Further, the apparatus 204 includes a catheter 221 (e.g., an example of the catheter 110 of FIG. 1), a processor 222, one or more position system(s) 223, a memory 224, and a transceiver 225, as well as mapping software 101.

According to an embodiment, the apparatus 204 can be an example of the system 100 of FIG. 1, where the apparatus 204 can include both components that are internal to the patient and components that are external to the patient. According to an embodiment, while a single apparatus 204 is shown in FIG. 2, example systems may include a plurality of apparatuses.

Accordingly, the apparatus 204, the local computing device 206, and/or the remote computing system 208 can be programed to execute computer instructions with respect to the mapping software 101. As an example, the memory 224 stores these instructions for execution by the processor 222 so that the apparatus 204 can receive and process the biometric data via the catheter 221. In this way, the processor 222 and the memory 224 are representative of processors and memories of the local computing device 206 and/or the remote computing system 208. It is possible for some or all of the mapping software 101 to exist and be executed by any of the apparatus 204, local computing device 206, and remote computing system 208.

The networks 210 and 211 can be a wired network, a wireless network, or include one or more wired and wireless networks. According to an embodiment, the network 210 is an example of a short-range network (e.g., local area network (LAN), or personal area network (PAN)). Information can be sent, via the network 210, between the apparatus 204 and the local computing device 206 using any one of various short-range wireless communication protocols, such as Bluetooth, Wi-Fi, Zigbee, Z-Wave, near field communications (NFC), ultra-band, Zigbee, or infrared (IR). Further, the network 211 is an example of one or more of an Intranet, a local area network (LAN), a wide area network (WAN), a metropolitan area network (MAN), a direct connection or series of connections, a cellular telephone network, or any other network or medium capable of facilitating communication between the local computing device 206 and the remote computing system 208. Information can be sent, via the network 211, using any one of various long-range wireless communication protocols (e.g., TCP/IP, HTTP, 3G, 4G/LTE, or 5G/New Radio). Note that for either network 210 and 211 wired connections can be implemented using Ethernet, Universal Serial Bus (USB), RJ-11 or any other wired connection and wireless connections can be implemented using Wi-Fi, WiMAX, and Bluetooth, infrared, cellular networks, satellite or any other wireless connection methodology.

In operation, the apparatus 204 can continually or periodically obtain, monitor, store, process, and communicate via network 210 the biometric data associated with the patient 202 and the position data of the catheter 110 (e.g., for the catheter electrodes 111 of the catheter basket 116). Further, the apparatus 204, local computing device 206, and the remote computing system 208 are in communication through the networks 210 and 211 (e.g., the local computing device 206 can be configured as a gateway between the apparatus 204 and the remote computing system 208). For instance, the apparatus 204 can be an example of the system 100 of FIG. 1 configured to communicate with the local computing device 206 via the network 210. The local computing device 206 can be, for example, a stationary/standalone device, a base station, a desktop/laptop computer, a smart phone, a smartwatch, a tablet, or other device configured to communicate with other devices via networks 211 and 210. The remote computing system 208, implemented as a physical server on or connected to the network 211 or as a virtual server in a public cloud computing provider (e.g., Amazon Web Services (AWS)®) of the network 211, can be configured to communicate with the local computing device 206 via the network 211. Thus, the biometric data associated with the patient 202 can be communicated throughout the system 200.

Elements of the apparatus 204 are now described. The catheter 221 is the catheter 110 of FIG. 1. The processor 222, in executing the mapping software 101, can be configured to receive, process, and manage the biometric data acquired by the catheter 221, and communicate the biometric data to the memory 224 for storage (e.g., on a database therein) and/or across the network 210 via the transceiver 225 (e.g., to a database thereof). Biometric data from one or more other apparatuses 204 can also be received by the processor 222 through the transceiver 225. The one or more position system(s) 223 include elements for detecting position of one or more elements of the catheter 110, such as the proximal end and distal end of the catheter basket 116. In some examples, the one or more position system(s) 223 includes a magnetic position detection system as described elsewhere herein. In some examples, the magnetic position detection system includes one or more reference electrodes, such as body surface electrodes or electrodes disposed on a bed. The reference electrodes are connected to a processing system (e.g., the processor 222). The reference electrodes communicate with position sensors of the catheter basket 116 to assist with determining position of those position sensors. In some examples, the position system(s) 223 include one or more other systems for detecting the positions for the catheter 110 (such as the positions of the proximal end and distal end of the catheter basket 116). The processor 222 interfaces with the position system(s) to obtain position data for the catheter 110. The mapping software 101 utilizes the position data to determine position of the electrodes 111 as described elsewhere herein.

In some examples, the position sensors 305 and 307 interface with a position sensing system according to a magnetic position detection technique. In some such examples, each position sensor includes three coils, each oriented in an orthogonal direction. Electrical current passing through each coil of each position sensor generates a magnetic field that is sensed by a location pad. In some examples, the location pad has at least three magnetic field generating corners, each having three orthogonally oriented coils that are configured to generate magnetic fields. Using the location pad, the position system 223 senses the magnetic signals emitted by the position sensors 305 and 307. The position system 223 utilizes the strength of the electrical signal received by the coils in each corner to triangulate the positions of each of the position sensors 305 and 307. The position system 223 uses the strengths of the signals received with the differently oriented sensors in the location pad to determine the orientation of the position sensors 305 and 307.

The memory 224 is any non-transitory tangible media, such as magnetic, optical, or electronic memory (e.g., any suitable volatile and/or non-volatile memory, such as random-access memory or a hard disk drive). The memory 224 stores the computer instructions for execution by the processor 222. The transceiver 225 may include a separate transmitter and a separate receiver. Alternatively, the transceiver 225 may include a transmitter and receiver integrated into a single device.

Figure 3A:
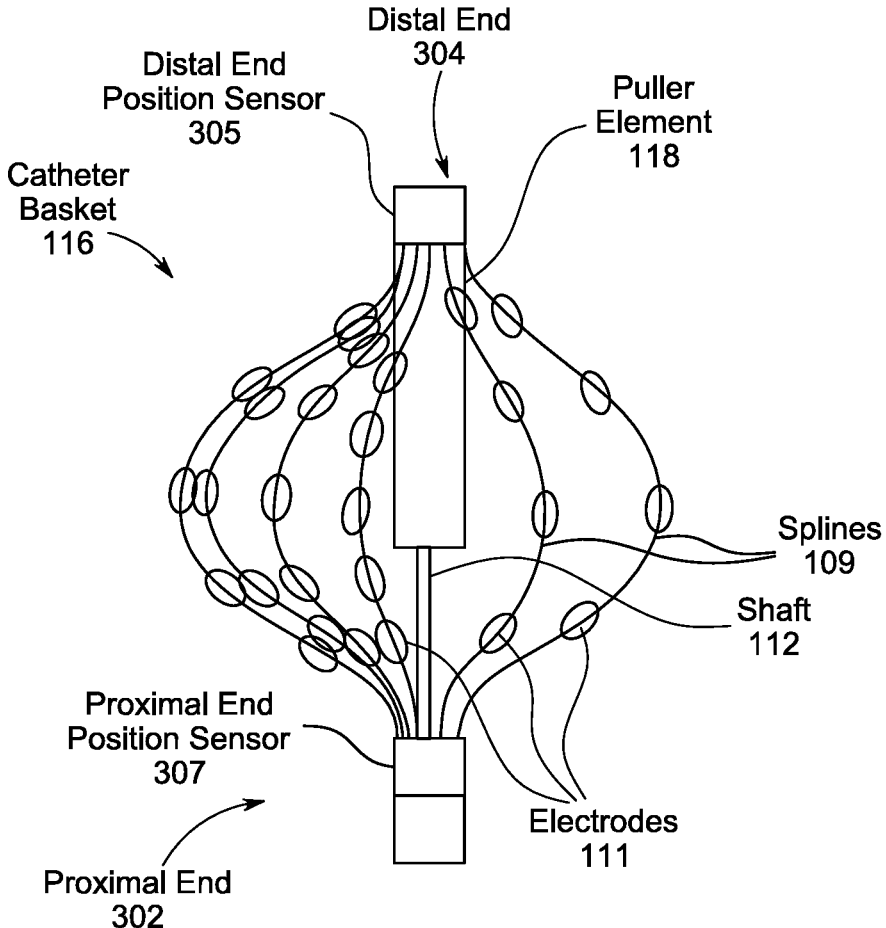
FIG. 3A illustrates a catheter basket, according to an example.

FIG. 3A illustrates a catheter basket 116, according to an example. The catheter basket 116 includes a shaft 112 coupled to a proximal end 302 of the catheter basket 116 and to a distal end 304 of a catheter basket 116. Splines 109 are coupled to a proximal end 302 and a distal end 304 of the catheter basket 116. Electrodes 111 are disposed on the splines 109. The proximal end 302 and distal end 304 are movable with respect to each other. A puller element 118, which is coupled to the distal end 304 of the catheter basket 116, can be pulled towards the proximal end 302 of the catheter basket to move the distal end 304 closer to the proximal end 302, or can be pushed from the proximal end 302 to move the distal end 304 farther from the proximal end 302. Moving the distal end 304 with respect to the proximal end 302 causes the splines 109 to deform. In addition, it is possible for the catheter basket 116 to be deflected at an angle with respect to the shaft 112 at the proximal end 302. In other words, it is possible for the basket assembly to bend at the proximal end 302, with respect to an "incoming angle" of the shaft 112. For example, when a part of the catheter basket 116 such as one or more of the splines 109 contacts anatomical structure, the catheter basket 116 deflects at an angle with respect to the shaft 112 at the proximal end 302. The shape of the splines 109 and thus the positions of the electrodes 111 thus depends on the relative positions of the proximal end 302 and the distal end 304, as well as the angle of deflection of the catheter 110 with respect to the shaft 112 at the proximal end 302. The proximal end 302 and distal end 304 each include one or more position sensors (the proximal end position sensor 307 and the distal end position sensor 305), so that mapping software 101 is able to determine their three-dimensional ("3D") positions directly (e.g., in conjunction with the position system(s) 223). However, the splines 109 do not have position sensors and, moreover, can change shape. For this reason, mapping software 101 estimates the positions and shapes of the splines 109 in order to use that information for mapping or ablation techniques as described herein.

Figure 3B:
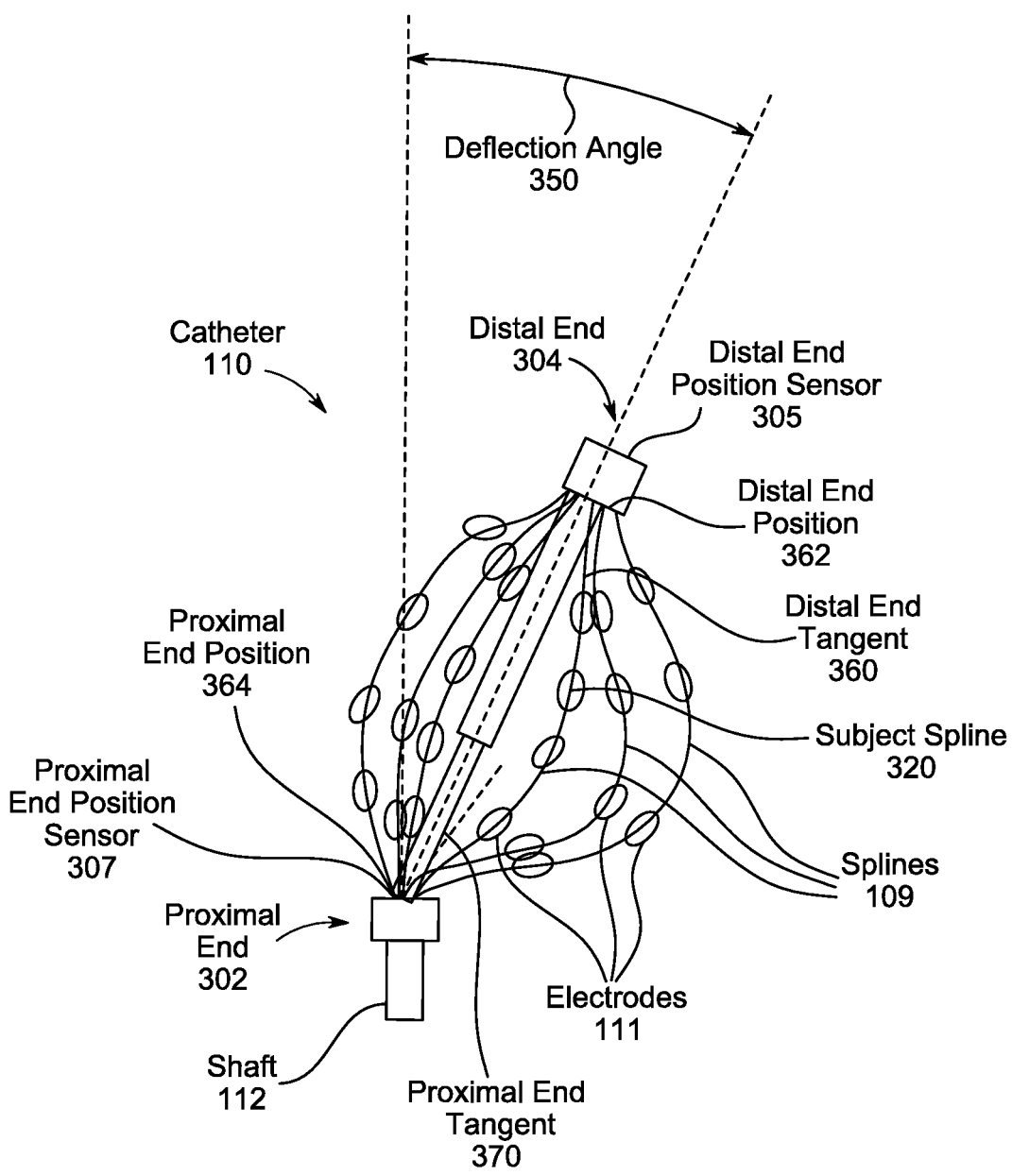
FIG. 3B illustrates a deflected catheter basket, illustrating inconsistent deformation across splines, according to an example.

FIG. 3B illustrates the catheter 110 in a deflected configuration. As can be seen, a portion of the shaft after to the proximal end 302 (the deflected portion of the shaft 112(1)) is deflected at an angle with respect to the portion of the shaft prior to the proximal end 302 (the undeflected portion of the shaft 112(2)). The splines 109 are bent in a certain way based on the angle of deflection. As shown, the catheter 110 is deflected to the right. Thus, the splines 109 on the right side experience pressure from the distal end 304 and proximal end 302 and thus extend further outward from the shaft 112 as compared with the splines 109 on the left side. The splines 109 on the left side are relatively more stretched out and thus are closer to the shaft 112 and to each other. The splines 109 on the left side are closer together as compared to the splines 109 on the right side, which are more spaced apart. The mapping software 101 uses these features of the geometry, along with the locations of the splines 109, to determine the shape of the splines 109 and the three-dimensional positions of the electrodes 111.

As described, the distal end position sensor 305 and proximal end position sensor 307 are capable of facilitating determination of the positions of the distal end 304 and proximal end 302, respectively. In some examples, the distal end position sensor 305 and proximal end position sensor 307, themselves, include mechanisms for determining orientation of the distal end position sensor 305 and the proximal end position sensor 307, and thus for determining angle of the shaft 112 with respect to the sheath 113. Such angle would simply be the angle reflected by the distal end position sensor 305 with respect to the angle reflected by the proximal end position sensor 307. In various examples, the proximal end position sensor 307 and distal end position sensor 305 include one or more electromagnetic components that emit signals reflective of the orientation of the sensors. A processing element such as the position system(s) 223 and/or the mapping software 101 is capable of receiving and interpreting the signals to identify the relative angles. In an alternative, one or more force sensors are present on the catheter 110. The one or more force sensors measure force applied to the catheter 110 and the direction of that force. A processing element such as the mapping software 101 is capable of determining the angle based on the measured force. In an example, the processing element modifies the measured force by a decay factor, reflecting the fact that as more deflection occurs, more force is needed for further deflection, to obtain the angle of deflection. Although several options for determining deflection angle are described, any technically feasible means for determining angle of deflection is possible. The processing element determines the shapes of the splines 109 based on the angle of deflection and the positions of the distal end 304 and the proximal end 302 as described elsewhere herein.

Figure 4:
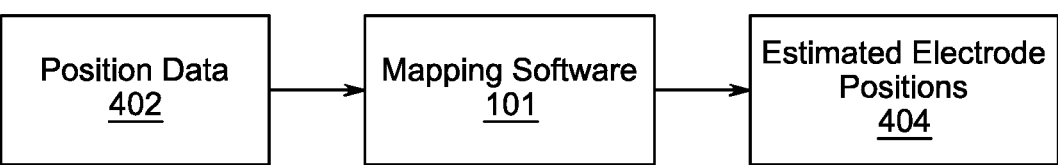
FIG. 4 illustrates operations for estimating the shape of the electrodes, according to an example.

FIG. 4 illustrates operations for estimating the shape of the splines 109, according to an example. The mapping software 101 accepts as input position data 402 (e.g., the locations of the proximal end 302 and distal end 304 of the catheter 110 and the deflection angle). The mapping software 101 estimates position and shape of the splines 109 using Bezier curves, and outputs the estimated electrode positions 404.

More specifically, the mapping software 101 receives information indicating the positions of the proximal end 302 and distal end 304, as well as the deflection angle. The mapping software 101 also accepts as input (e.g., as a set of stored constants or as input from another software module executing in the system 200) the known length of the splines 109, as well as the tangent of the splines 109 at the proximal end. The mapping software 101 then calculates the Bezier curve defining the shape of the splines 109 in the following manner:

$$B(t) = \sum_{i=0}^{n} \binom{n}{i} (1-t)^{n-1} t^i P_i$$

In the above equation, B(t) represents the Bezier curve. Value t is the input value to the function B defining the curve. Value t varies along the curve itself and represents the projection of the curve onto a horizontal axis. Value $P_i$ is the i-th Bezier curve control point. The notation $$\binom{n}{i}$$

refers to the binomial coefficients. n is the number of control points and i is the summation index for the summation operation. The polygon formed by connecting the Bezier control points with lines is called the Bezier polygon. The convex hull of the Bezier polygon contains the Bezier curve. $P_0$ and $P_n$ are the coordinates of the proximal end 302 and known length of the spline. $P_1$ and $P_{n-1}$ are defined by the tangents of the splines 109 at the proximal end 302 and distal end 304. Mapping software 101 selects the other control points based on conservation of energy considerations. It is assumed that when the splines 109 bend, they will bend in a manner that uses minimum spring energy.

The mapping software 101 determines the control points for the Bezier curve as described and then estimates the shape of the splines 109 using the function B(t). Note that the control points do not necessarily lie on the curve but define the curve. The curve order of a Bezier curve is defined as the number of control points minus one.

As stated above, B(t) describes the curve defined by the control points of the Bezier curve. In some examples, the mapping software 101 discretizes a calculated curve shape into several "geometric points." The geometric points define the shape of the splines 109. These geometric points are points that sit on the curve that defines the shape of the splines and, again, are distinct from the control points that parameterize the Bezier curves. Based on the shapes and positions of the splines 109, the mapping software 101 determines the positions of the electrodes 111. For example, the mapping software 101 knows how far along each splines 109 each electrode 111 lies. The mapping software 101 the shapes of the splines 109, the mapping software 101

In some examples, the mapping software 101 incorporates the estimated positions of the electrodes 111 into the mapping and/or ablation operations. In some examples, the mapping software 101 or other software uses the estimated positions to draw the electrodes onto a screen or image for viewing by a human operator. In some examples, this image is combined with other imagery to illustrate the electrodes 111 and other equipment such as the remainder of the catheter 110 in the context of a clinical environment such as what is shown in FIG. 1. In some examples, the mapping software 101 also includes the estimated shapes of the splines 109 in the display, so that the display output illustrates the positions and shapes of the splines 109 as well as the positions of the electrodes 111 disposed on those splines 109. In various examples, being able to determine the positions of the electrodes 111 facilitates mapping and ablation operations. More specifically, with the positions of the electrodes 111, it is possible to accurately map the locations of actions performed with the electrodes 111 to positions relative to anatomical structures. This information thus allows accuracy for a doctor or for a computer system involved with a procedure. In an example where mapping is occurring, the mapping software 101 obtains measurements with the electrodes 111 that reflect aspects of nearby anatomy being mapped. In examples, these measurements reflect relative distance or position of anatomical structures to the electrodes 111. By knowing the positions of the electrodes 111, the mapping software 101 is able to accurately determine geometric features of the anatomical structures. More specifically, the mapping software 101 determines geometric features of the anatomical structures by combining the information sensed with the electrodes 111 about the relative geometry of anatomical structures with the information of the estimated electrode 111 positions to obtain the geometry of the anatomical structures.

Figure 5:
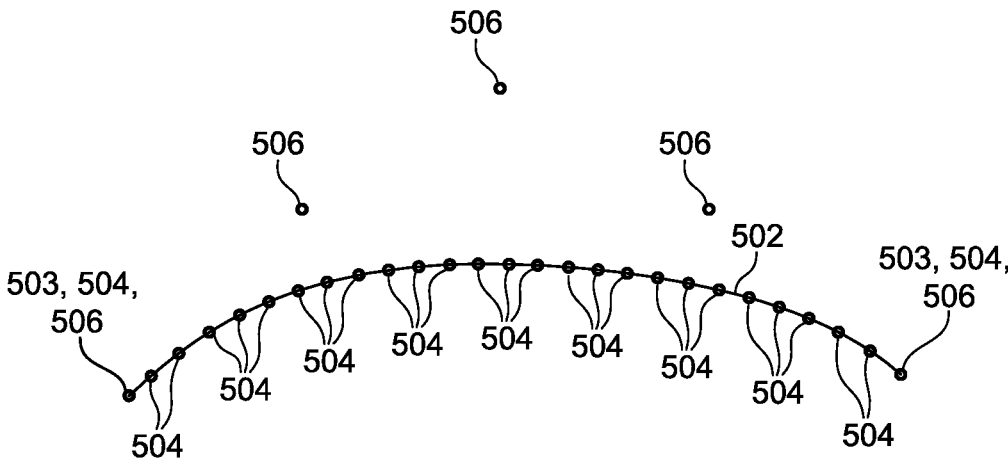
FIG. 5 illustrates an estimated electrode shape, according to an example.
Figure 6:
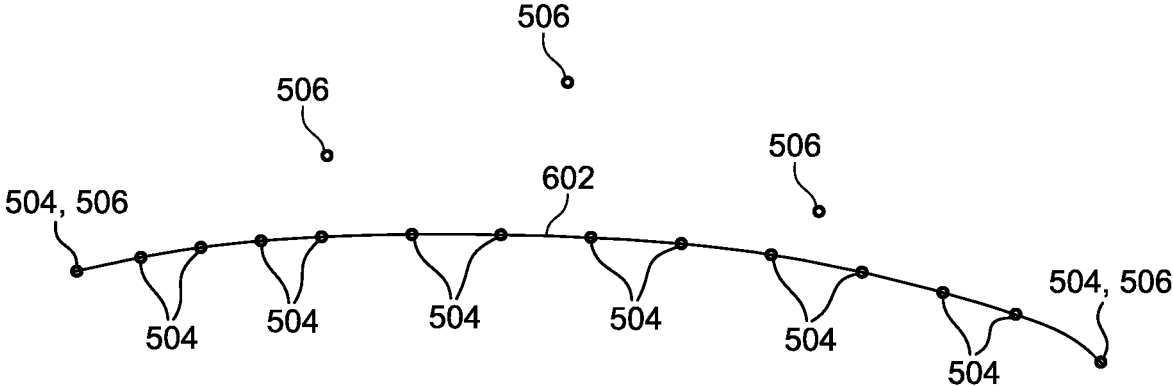
FIG. 6 illustrates an estimated electrode shape that is different than the estimated electrode shape of FIG. 5, according to an example.

FIGS. 5 and 6 illustrate aspects of processing for estimating shapes of individual splines 109, according to an example. FIG. 5 illustrates an estimated spline shape 502, according to an example. In addition, geometry points 504 and Bezier curve control points 506 are illustrated as well. Endpoint locations 503 (e.g., positions of the proximal end 302 and distal end 304) illustrate the endpoints of the splines 109.

The mapping software 101 determines the control points 506 of the Bezier curve in any technically feasible manner, such as in a manner described herein. More specifically, the mapping software 101 calculates the control points 506 based on the relative locations of the endpoint locations 503 as well as the deflection angle of the catheter 110. Then, the mapping software 101 generates the geometry points 504 based on the control points 506. The geometry points 504 define the actual shape of the curve. In some implementations, the mapping software 101 also utilizes the geometry points 504 to assist with mapping and/or ablation operations. In some examples, the mapping software 101 determines the positions of the electrodes 111 disposed on the splines 109 based on the estimated shapes and positions of the splines 109, and utilizes the electrode positions for the mapping and/or ablation operations. In some implementations, the mapping software 101 or other software or hardware uses the geometry points 504 to generate an image, which can be used to display the shapes and positions of the splines 109 and/or the positions of the electrodes 111.

FIG. 6 illustrates an estimated spline shape 602 that is different than the estimated spline shape 502 of FIG. 5. In FIG. 6, the angle of deflection of the catheter 110 is different than the angle in FIG. 5. Thus, the estimated spline shape 602 is different than in FIG. 5. The positions of the Bezier curve control points define the curve, and the curve is shown as falling along a set of geometry points 504.

Referring back to FIG. 3B, the mapping software 101 utilizes the tangents of the splines 109 at the proximal end and length of the spline, as well as the positions of the proximal end and distal end, to determine the shapes of the splines 109 using Bezier curves. In FIG. 3B, a subject spline 320 is illustrated as an example, to illustrate aspects of the technique. However, it should be understood that in various implementations, the mapping software 101 applies the described technique to one, more than one, or all splines 109 of a catheter basket 116 to determine shapes of those splines 109 and thus the positions of the electrodes 111 on those splines 109.

In some examples, the mapping software 101 generates a Bezier curve that describes the shape and three-dimensional positions of the splines 109. The Bezier curve is a fourth order Bezier curve that accepts at least four constraints to generate the control points. The four constraints include the position of the distal end of the spline (shown as the distal end position 362 for the subject spline 320), the position of the proximal end of the spline (shown as the proximal end position 364 for the subject spline 320), the known length of the spline, and the tangent of the spline at the proximal end (shown as proximal end tangent 370 for subject spline 320). Based on the above four constraints, the mapping software 101 determines the Bezier curve control points. The mapping software 101 determines the shape of the splines 109 for which the control points are determined as disclosed elsewhere herein (e.g., according to the equation provided above). Using this shape and the positions of the proximal and distal ends of the splines (which are, e.g., determined based on the positions detected via the distal end position sensor 305 and proximal end position sensor 307), the mapping software 101 determines the positions of the splines 109 within the surrounding three-dimensional space (e.g., the three-dimensional space of the heard 120 or other anatomical structure(s)).

The mapping software 101 determines the positions of the electrodes 111 on each spline 109 for which the shape and position has been determined, based on the positions and shapes of the splines 109. In an example, the mapping software 101 knows how far along each spline 109 the electrodes are places. For example, the mapping software 101 is provided with information that the electrodes are placed at particular distances along the splines 109. These distances may be expressed in any technically feasible manner, which as with a percentage of the length of the spline 109. In an example, the electrodes are placed every 10% increment along the spline 109. The mapping software 101 may use any other technically feasible technique to associate the positions of the electrodes 111 with positions along the splines 109.

The mapping software 101 determines the three-dimensional position of each electrode 111 based on this association between the positions of the electrodes 111 and the positions of the splines 109, and based on the shape and position of the splines 109 determined using the Bezier curves. In an example, the Bezier curve formula defines a position B with respect to a projected-axis coordinate t. Thus, in some examples, the mapping software 101 determines the position of an electrode 111 in three-dimensional space, given the position along the spline 109 at which the electrode is located. For example, for an electrode that is located 10% of the way from the proximal end to the distal end, the mapping software 101 uses 10% as the t coordinate, to determine the on-curve coordinate B for that electrode. In some examples, the technique of determine electrode 111 position based on the distance along the spline 109 of the electrode and the shape and position of the electrode 111 is referred to herein as interpolating. For example, it may sometimes be stated that the mapping software 101 determines the position of the electrode 111 by interpolating the curve of the spline 109 according to the position along the spline 109 that the electrode 111 lies. The mapping software 101 then transforms this coordinate based on the location of the spline 109 in three-dimensional space (e.g., the proximal end location and distal end location) to determine the location of the electrode 111 in three-dimensional space. The mapping software 101 performs these operations for one, more than one, or all splines 109 of a catheter basket 116 to determine the positions for one, more than one, or all electrodes 111 of the catheter basket 116.

It is sometimes stated that the deflection angle is considered in determining the positions and/or shapes of the splines 109. The deflection angle determines the tangent of the distal end (e.g., distal end tangent 360), since the splines 109 bend as the distal portion of the shaft 112(1) bends. Thus, since the Bezier curve control points are determined based at least in part on the spline tangent at the distal end 304, the Bezier curve control points are determined based at least in part on the deflection angle 350.

Once found, the apparatus 204 (e.g., in conjunction with the local computing device 206 and/or the remote computing system 208) utilizes the electrode 111 positions to perform mapping and/or ablation procedures. With the electrode 111 positions, the system 204 is able to place the electrodes 111 in the three-dimensional space of surrounding anatomical structures, which allows for the ablation and/or mapping procedures to proceed using this information. For example, knowing the position of the electrodes 111 allows electrical signals obtained via the electrodes 111 that indicate proximity to anatomical structures to be converted to positions of the anatomical structures. Additionally, for an ablation procedure, knowing the positions of the electrodes 111 in three-dimensional space allows for knowledge of what portions of the anatomical structures is to be ablated.

Figure 3C:
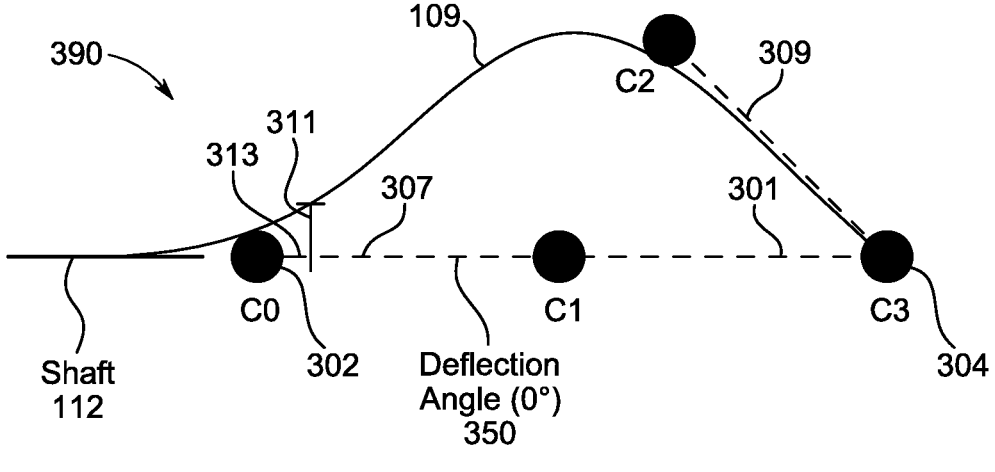
FIG. 3C illustrates a spline in a non-deflected position, according to an example.
Figure 3D:
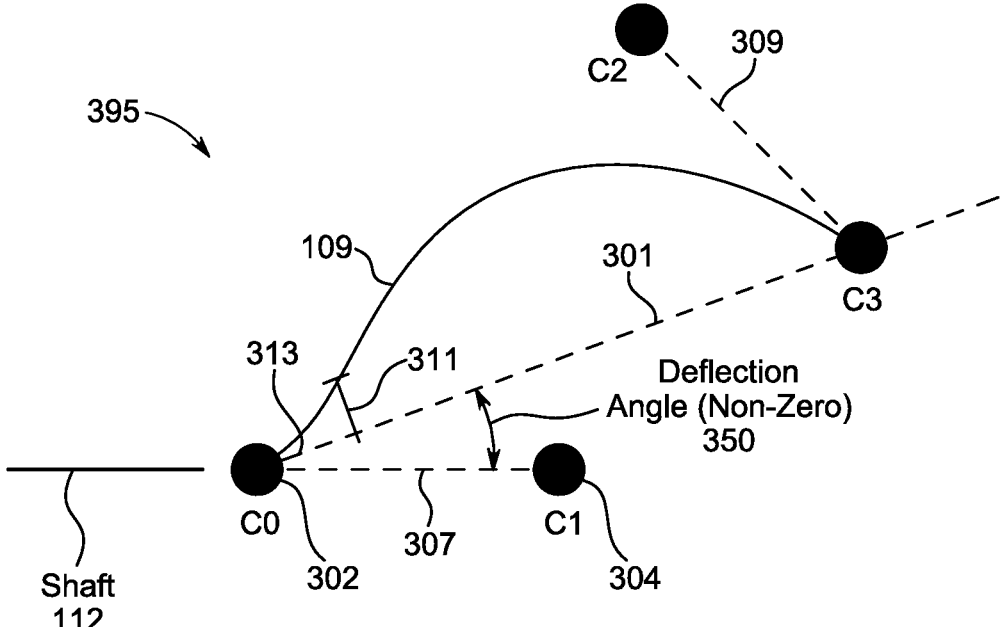
FIG. 3D illustrates a spline in a deflected position, according to an example.

FIGS. 3C and 3D illustrate operations for utilizing Bezier curves to estimate spline shape, according to an example. FIG. 3C illustrates a spline 390 in an undeflected position. FIG. 3D illustrates a spline 395 in a deflected position. In FIG. 3C, the spline 390 is in an undeflected position. This means that the angle 350 between the incoming shaft 112 and the ray 301 between the proximal end 302 and the distal end 304 is 0. In FIG. 3D, the spline 395 is in a deflected position. This means that the angle 350 between the incoming shaft 112 and the ray 301 between the proximal end 302 and the distal end 304 is an angle other than 0. In both FIG. 3C and FIG. 3D, points C0 through C3 represent the Bezier curve control points.

As stated elsewhere herein, the mapping software 101 determines the positions of the Bezier curve control points based on the positions of the proximal end 302 and the distal end 304, as well as the deflection angle 350 and the tangent of the spline 109 near to the proximal end 302 and known length of the spline. In both FIG. 3C and FIG. 3D, the proximal end tangent 307 is the tangent of the spline 109 at the proximal end 302 and the distal end tangent 309 is the tangent of the spline 109 at the distal end 304. The proximal end tangent 307 is in line with and parallel to the incoming shaft 112 due to the way the spline 109 is fastened to the shaft. At the distal end, the coupling to the spline 109 acts as a hinge and thus the distal end tangent 309 is able to move as illustrated.

The mapping software 101 uses an iterative technique to determine the positions of the Bezier curve control points. Specifically, while C0 and C3 are fixed—that is, these points are the points of the proximal end 302 and the distal end 304, respectively—the points C1 and C2 are chosen to further define the curve. The mapping software 101 selects point C1 to keep the splint 109 lower than a height threshold 311 at a distance 313 from the proximal end 302. The distance 313 is measured along the ray 301 between the proximal end 302 and the distal end 304. The height 311 is perpendicular to that ray 301. The mapping software 101 selects point C2 to keep the length of the spline 109 to approximately equivalent to the actual length of the spline 109 on which the spline 109 is modeled. The mapping software 101 also selects point C2 to keep the radius of the spline 109 below a maximum radius. In sum, the mapping software 101 selects points C0 and C3 based on the actual positions of the proximal end 302 and the distal end 304 and selects points C1 and C2 based on the physical constraints of the tangent of the spline 109 at the proximal end 302, the tangent of the spline 109 at the distal end 304, the height 311, and the maximum radius. In some examples, the mapping software 101 selects points C1 and C2 iteratively. More specifically, the mapping software 101 initially selects point C1 arbitrarily along the ray between point C0 and C3, and initially selects the position of point C2 arbitrarily, with the limitation that the spline 109 shape is below the radius threshold. The mapping software 101 tests the various limitations, including the length of the spline 109 and the height 311. If those limitations are not appropriate, then the mapping software 101 selects different points for C1 and C2. The limitations are appropriate if the length of the spline 109 is within a threshold percentage of the actual length of the physical spline 109 and if the height 311 is below a predetermined threshold. If the limitations are appropriate, then the mapping software 101 has determined a shape for the spline 109. It should be understood that the mapping software 101 applies the technique described with respect to FIGS. 3C and 3D to multiple splines 109 of a catheter, to determine shape and location of those splines 109.

Figure 7:
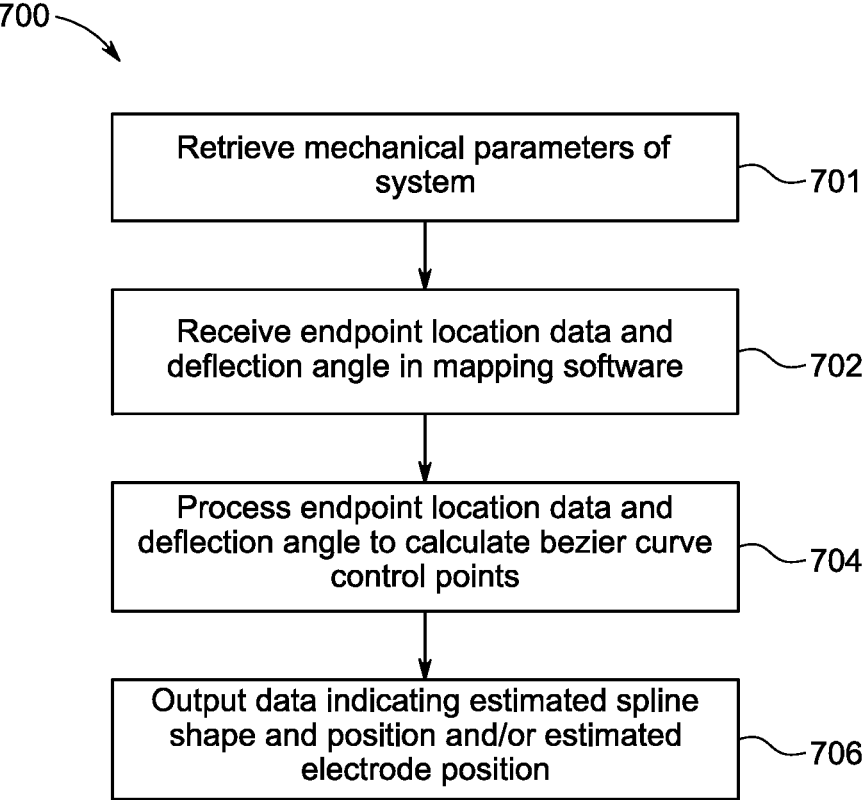
FIG. 7 is a flow diagram of a method for estimating electrode shape for a basket catheter, according to an example.

FIG. 7 is a flow diagram of a method 700 for estimating geometry information for a basket catheter, according to an example. Although described with respect to the systems of FIGS. 1-6, those of skill in the art will understand that any system, configured to perform the operations of the method 700 in any technically feasible order, falls within the scope of the present disclosure.

At step 701, the mapping software 101 retrieves mechanical constraints for the basket 116 and/or splines 109. In some examples, the mechanical constraints are the tangent of the spline 109 at the proximal end and the known length of the spline.

At step 702, the mapping software 101 receives endpoint location data and deflection angle for a catheter basket 116. In some examples, the endpoint location data is data that specifies the positions of the proximal end 302 and distal end 304 of the basket catheter 110. In some examples, the deflection angle indicates the deflection of the basket catheter 110 with respect to angle of the shaft 112. In some examples, the mapping software 101 receives or determines the tangents of the splines 109 at the proximal end 302 and at the distal end 304, and in some examples, at least the tangents of the splines 109 at the distal end 304 are based on the deflection angle 350.

At step 704, the mapping software 101 processes the endpoint location data, the tangent of the spline at the proximal end and the estimate length of the spline to calculate Bezier curve control points. As described above, the control points for the Bezier curves define the geometry of the curves, but do not necessarily sit on the curves themselves.

In some examples, the mapping software 101 also calculates the geometry points 504 that define the estimated shapes of the splines 109 based on the Bezier curve control points. While the Bezier curve control points do not sit on the actual curve, but only define that curve, the geometry points 504 sit on the curve and define the curve as a collection of points that fall on that curve.

At step 706, the mapping software 101 outputs data indicating estimated spline positions and shapes and/or estimated electrode positions. In some examples, the mapping software 101 outputs the data for display on a display to be viewed by a user. Alternatively or additionally, the mapping software 101 exports this data for use in mapping or ablation procedures.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. A computer readable medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire Examples of computer-readable media include electrical signals (transmitted over wired or wireless connections) and computer-readable storage media. Examples of computer-readable storage media include, but are not limited to, a register, cache memory, semiconductor memory devices, magnetic media such as internal hard disks and removable disks, magneto-optical media, optical media such as compact disks (CD) and digital versatile disks (DVDs), a random access memory (RAM), a read-only memory (ROM), an erasable programmable read-only memory (EPROM or Flash memory), a static random access memory (SRAM), and a memory stick. A processor in association with software may be used to implement a radio frequency transceiver for use in a terminal, base station, or any host computer.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The descriptions of the various embodiments herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A method for improving cardiac mapping during a cardiac procedure, the method comprising:
   receiving endpoint location data during the cardiac procedure based on measurements taken with a first sensor mounted at a proximal end of a distal tip of a catheter and a second sensor mounted at a distal end of the distal tip, wherein the distal tip includes a plurality of flexible splines each coupled to a plurality of electrodes;
   determining a deflection angle of the second sensor relative to a longitudinal axis of the distal tip;
   determining spline tangent data comprising, for each of the plurality of flexible splines, a tangent at a proximal portion of the spline;
   determining, for each of the plurality of flexible splines, a tangent at a distal portion of the spline based on the deflection angle using a stored mapping between a circumferential anchor index of the spline and a deflection frame of the second sensor;
   for each of the plurality of flexible splines, calculating control points of a respective Bezier curve based on the endpoint location data, the proximal-portion tangent from the spline tangent data, and the distal-portion tangent determined from the deflection angle, wherein each respective Bezier curve has the proximal end and the distal end of the distal tip as endpoints and is solved by enforcing (i) the proximal-portion and distal-portion tangents as endpoint tangent constraints and (ii) an arc-length constraint equal to a known length of the corresponding flexible spline, and wherein calculating the control points is performed without using electrode positions as fit points;
   determining estimated positions of each of the plurality of electrodes based on the calculated control points; and
   displaying, during the cardiac procedure, an electro-anatomical map of a heart chamber based on the estimated positions.

2. The method of claim 1, wherein the distal tip is a catheter basket, wherein the endpoint location data comprises locations of the proximal end and the distal end of the distal tip, and wherein each respective Bezier curve uses the proximal end and the distal end as its endpoints.

3. The method of claim 1, wherein determining the tangent at the distal portion based on the deflection angle is performed for each of the plurality of flexible splines using the stored mapping between the circumferential anchor index and the deflection frame.

4. The method of claim 1, wherein the known length is a known length of each of the plurality of flexible splines as used to enforce the arc-length constraint for the respective Bézier curves in claim 1.

5. The method of claim 1, wherein determining:
   the estimated positions of the plurality of electrodes comprises generating geometry points from the respective Bézier curve control points and determining the estimated electrode positions by arc-length parameterization along each respective curve based on stored along-spline electrode indices.

6. The method of claim 1, wherein the first sensor and the second sensor each comprise a magnetic position sensor configured to sense position in three dimensions.

7. The method of claim 1, wherein the endpoint location data includes locations of the first sensor and the second sensor, and wherein calculating the control points for each respective Bézier curve uses the locations of the first and second sensors as the endpoints of the curve.

8. The method of claim 1, wherein calculating the control points and determining the estimated positions are performed without using any electrode electrical measurements, including impedance-based or electrogram-derived positions, as fit points.

9. A system for improving cardiac mapping during a cardiac procedure, the system comprising:
   a communication interface that is communicatively coupled to a catheter that includes a first sensor mounted at a proximal end of a distal tip of the catheter and a second sensor mounted at a distal end of the distal tip, wherein the distal tip includes a plurality of flexible splines each coupled to a plurality of electrodes;
   a display;
   a memory; and
   one or more processors communicatively coupled to the communication interface, the display, and the memory, the one or more processors collectively configured to:
      receive, using the communication interface and during the cardiac procedure, endpoint location data based on measurements taken with the first sensor and the second sensor while the distal tip is positioned within a heart chamber;

determine a deflection angle of the second sensor relative to a longitudinal axis of the distal tip;

determine spline tangent data comprising, for each of the plurality of flexible splines, a tangent at a proximal portion of, the spline;

determine, for each of the plurality of flexible splines, a tangent at a distal portion of the spline based on the deflection angle using a stored mapping between a circumferential anchor index of the spline and deflection frame of the second sensor;

for each of the plurality of flexible splines, calculate control points of a respective Bezier curve based on the endpoint location data, the proximal-portion tangent from the spline tangent data, and the distal-portion tangent determined from the deflection angle, wherein each respective Bezier curve has the proximal end and the distal end of the distal tip as endpoints and is solved by enforcing (i) the proximal-portion and distal-portion tangents as endpoint tangent constraints and (ii) an arc-length constraint equal to a known length of the corresponding flexible spline, and wherein calculating the control points is performed without using electrode positions as fit points;

determine estimated positions of each of the plurality of electrodes based on the calculated control points; and render, during the cardiac procedure, an electro-anatomical map of the heart chamber on the display based on the estimated positions.

10. The system of claim 9, wherein the distal tip is a catheter basket, wherein the endpoint location data comprises locations of the proximal end and the distal end of the distal tip, and wherein each respective Bézier curve uses the proximal end and the distal end as its endpoints.

11. The system of claim 9, wherein the one or more processors are further configured:

such that determining the tangent at the distal portion based on the deflection angle is performed for each of the plurality of flexible splines using the stored mapping between the circumferential anchor index and the deflection frame.

12. The system of claim 9, wherein each respective Bezier curve is constrained to the known length of the corresponding flexible spline as recited in claim 8, the known length being stored in the memory.

13. The system of claim 9, wherein determining the estimated positions of the plurality of electrodes comprises generating geometry points from the respective Bezier curve control points and determining the estimated electrode positions:

by arc-length parameterization along each respective curve based on stored along-spline electrode indices.

14. The system of claim 9, wherein the first sensor and the second sensor each comprise a magnetic position sensor configured to sense position in three dimensions.

15. The system of claim 14, further comprising a location pad fixedly located outside of a patient in which the catheter is inserted, wherein the location pad is configured to generate magnetic fields that are sensed by the magnetic position sensors.

16. A non-transitory computer-readable medium storing instructions for improving cardiac mapping during a cardiac procedure, the instructions when collectively executed by one or more processors of a console, cause the console to perform operations comprising:

receiving endpoint location data during the cardiac procedure based on measurements taken with a first sensor mounted at a proximal end of a distal tip of a catheter and a second sensor mounted at a distal end of the distal tip, wherein the distal tip includes a plurality of flexible splines each coupled to a plurality of electrodes;

determining a deflection angle of the second sensor relative to a longitudinal axis of the distal tip;

determining spline tangent data comprising, for each of the plurality of flexible splines, a tangent at a proximal portion of the spline;

determining, for each of the plurality of flexible splines, a tangent at a distal portion of the spline based on the deflection angle using a stored mapping between a circumferential anchor index of the spline and a deflection frame of the second sensor;

for each of the plurality of flexible splines, calculating control points of a respective Bezier curve based on the endpoint location data, the proximal-portion tangent from the spline tangent data, and the distal-portion tangent determined from the deflection angle, wherein each respective Bézier curve has the proximal end and the distal end of the distal tip as endpoints and is solved by enforcing (i) the proximal-portion and distal-portion tangents as endpoint tangent constraints and (ii) an arc-length constraint equal to a known length of the corresponding flexible spline, and wherein calculating the control points is performed without using electrode positions as fit points;

determining estimated positions of each of the plurality of electrodes based on the calculated control points; and displaying, during the cardiac procedure, an electro-anatomical map of a heart chamber based on the estimated positions.

17. The non-transitory computer-readable medium of claim 16, wherein the distal tip is a catheter basket, and wherein the endpoint location data comprises locations of the proximal end and the distal end of the distal tip.

18. The non-transitory computer-readable medium of claim 16, wherein determining the tangent at the distal portion based on the deflection angle is performed for each of the plurality of flexible splines using the stored mapping between the circumferential anchor index and the deflection frame.

19. The non-transitory computer-readable medium of claim 16, wherein each respective Bézier curve is constrained to the known length of the corresponding flexible.

20. The non-transitory computer-readable medium of claim 16, wherein determining the estimated positions of the plurality of electrodes comprises generating geometry points from the respective Bézier curve control points and determining the estimated electrode positions by arc-length parameterization along each respective curve based on stored along-spline electrode indices.

* * * * *